United States Patent [19]

Perry et al.

[11] Patent Number: 5,057,197
[45] Date of Patent: Oct. 15, 1991

[54] PROCESS AND APPARATUS FOR THE REMOVAL OF UNDESIRED COMPONENTS FROM AQUEOUS FEEDSTOCKS

[75] Inventors: Mordechai Perry, Petach Tikva; Reuven Katraro, Rishon Lezion; Charles Linder, Rehovot, all of Israel

[73] Assignee: Membrane Products Kiryat Weizmann Ltd., Rehovot, Israel

[21] Appl. No.: 348,802

[22] Filed: May 8, 1989

[30] Foreign Application Priority Data

May 9, 1988 [IL] Israel ......................................... 86319

[51] Int. Cl.$^5$ ............................................. B01D 13/02
[52] U.S. Cl. .................................. 204/182.4; 204/801; 204/182.3
[58] Field of Search ................... 204/182.4, 182.3, 301

[56] References Cited

U.S. PATENT DOCUMENTS

| | | | |
|---|---|---|---|
| 3,752,743 | 8/1973 | Henshilwood | 195/127 |
| 3,752,749 | 8/1973 | Chlanda et al. | 204/182.4 |
| 4,031,251 | 6/1977 | Margolis et al. | 426/427 |
| 4,554,076 | 11/1985 | Speaker | 210/639 |
| 4,758,319 | 7/1988 | Klinkowski | 204/182.3 |
| 4,781,809 | 11/1988 | Falcone, Jr. | 204/182.4 |

FOREIGN PATENT DOCUMENTS

| | | | |
|---|---|---|---|
| 52686 | 8/1977 | Israel | 204/182.6 |
| 52687 | 8/1977 | Israel | 204/182.6 |

OTHER PUBLICATIONS

Glover, F. A., "Ultrafiltration and Reverse Osmosis for the Dairy Industry", The National Institute for Research in Dairying, Technical Bulletin 5, 1985.
Assar.FCOJ, 19th Annual Short Course for Food Industry, 1979.
Breton, Dissertation Abstracts, 1958, 18:822.
Marshall et al., Food Technol. 1968 (22):969.
Johnson & Chandler, CSIRO Food Res. Q.1985:4525-32.

Primary Examiner—John F. Niebling
Assistant Examiner—Arun S. Phasge
Attorney, Agent, or Firm—Ladas & Parry

[57] ABSTRACT

An efficient process and system for the removal of at least one organic acid from aqueous feed streams.

24 Claims, 1 Drawing Sheet

PROCESS AND APPARATUS FOR THE REMOVAL OF UNDESIRED COMPONENTS FROM AQUEOUS FEEDSTOCKS

FIELD OF THE INVENTION

The present invention relates to a process and apparatus for removing undesired components and especially organic acids from aqueous feedstocks containing them.

BACKGROUND OF THE INVENTION

It is frequently desired to separate organic acids from feedstocks containing them. The term "feedstocks" as used herein is intended to denote aqueous media generally, whether solutions or suspensions, which have an undesired content of organic acids. Such media include, for example, process liquids and waste streams from the food industry, or from chemical production plants utilizing synthetic or extractive methods, or biotechnological methods. In the known art, the following techniques have been used to effect such separations, namely, ion exchange, solvent extraction, absorption with selective resins, extraction with supercritical gases, and the action of membranes.

When effecting such separations, it is often desired to otherwise maintain the composition of the aqueous feedstocks substantially unchanged. By way of example, it may be noted that absorptive processes in which citrus juices were contacted with ion exchange resins, have been used to remove citric acid and the bitterness due to limonin, therefrom (Johnsson and Chaundler, CSIRO Food Res. Q. 1985: 4525-32); most of the absorbents used in these processes did not absorb juice sugars, had no adverse effect on the fruit character of the juices and in particular did not introduce objectionable off flavors. The main problem observed during the processing of orange juice related to the slight loss of vitamins, minerals and amino acids; see Assar, Minute Maid Reduced Acid, FCOJ, 19th annual short course for the food industry, 1979. Moreover, adsorption processes require regeneration of the absorbent, resulting in the use of chemicals, consumption of energy and a waste disposal problem for the regenerating chemicals.

Selective separations using membranes offer considerable advantages over other known separation processes. Thus, they can readily be adapted to a commercial scale and to continuous operation, they do not require the use of regenerating chemicals and offer substantial economic advantages. For these reasons, conventional separation techniques are being increasingly replaced by techniques utilizing selective membranes. Such techniques include reverse osmosis (RO), ultrafiltration (UF) and microfiltration (MF), all of which are pressure driven, and electrodialysis (ED), which as the name implies is electrically driven.

In RO, UF and MF, a liquid stream containing soluble and suspended matter is circulated parallel to the membrane surface (cross flow) and pressurized simultaneously. Water and some soluble substances are transported across the membrane, while the retained soluble and suspended substances are concentrated. These processes differ in the dimensions of the membrane pores: in UF membranes they may range from 1.5 to 100 nanometers, in MF membranes from 0.05 microns to 10 microns, while in RO membranes they may range from 0.1 to 1.0 nanometers. Thus UF is basically a sieving process—the small molecules are responsible for the established osmotic pressure but are not retained by the membrane, the applied hydraulic pressures are thus not high; they may be of the order of about 5 bars, as compared with the higher pressures of say 10 to 100 bars in the case of RO.

Diafiltration (DF) is a modification of pressure driven processes (mainly UF and MF) in which water is added to the feed, to maintain its volume constant. As filtration proceeds, the components are effectively washed out from the feed and pass through the membrane, the rate of adding water to the feed equals the rate of permeate removal. The diluted permeate stream is regarded as waste and is often discarded.

In ED, a feed containing ionized species is circulated in a stack of alternating cation and anion exchange membranes under an applied electric field, so that the ionized species are transported from the feed into the adjacent compartments. Ion exchange membranes have pores of the order of inorganic and relatively small organic ions; inorganic ions in particular can be effectively removed by this process. In the case of small organic ions having a molecular weight below 200, these can also be readily removed by means of ED in the absence of fouling agents, but if large organic ions above 400 daltons are present they plug the membrane pores with the result that the process becomes very inefficient. Thus, there are relatively few successful commercial applications of ED where organic ions are involved.

As indicated above, unit separation processes such as UF, MF and RO are being increasingly applied in the food industry, e.g. for concentrating liquid products. Such processes are especially beneficial for products which would be adversely affected by high temperatures, and are also energy efficient. In this connection, reference may be made, for example, to "Water and ion flow-through imperfect osmotic membranes", Breton E. J., Dissertation Abstr. 18: 822 (1958). Applications of UF and RO for concentrating liquid food products were initiated in the dairy industry in the 1960s. Marshall et al in Food Technol. 22: 969 (1968), studied the concentration of cottage cheese whey solids by RO as an alternative to whey disposal. Industrial scale applications of UF and RO in the dairy industry are summarized by Glover, National Institute for Dairying, Reading, England, 1985. Other studies described UF and RO concentrating techniques for concentrating various liquid food products such as maple syrup, egg white, fruit and vegetable juices, and plant pigments such as anthocyanins. In general, these researches concluded that such techniques, modified as necessary, could be applied to the food industry.

A combined UF and RO process is also known in the literature for the preparation of purified beet color extracts, which were separated from soluble solids originally present in the feed. The juices were prefiltered, enzymated and subjected to a two stage UF process, using in sequence UF membranes with 20,000 and 6000 molecular weight cutoff, in order to remove soluble materials of high molecular weight. Such materials, if present in a stream contacting RO membranes, would plug the pores and therefore reduce the throughput rates and recovery of the natural color. In order to recover as much as possible of the natural color in the permeate of each UF step, the feed was repeatedly diluted and washed out with fresh water. In the subsequent RO step, the solution was subjected to combined concentration and purification, the RO membrane being endowed with high retention of the color, while allowing inorganic salts, sugars and beet taste components to permeate. A highly concentrated beet color product with improved sensory properties was thus obtained. In this example, UF and RO membranes were used to fractionate a selected component from an aqueous stream; all fractions except the color were of minor value and could be discarded. It is to be noted that large quantities of rinsing water were used for extracting the color while removing high molecular weight contaminants in the UF steps, without losing the color when low molecular weight contaminants were being removed in the subsequent RO step. In such a process, the high dilution of the permeate solubles means that their recovery is not usually economic and they are lost in the discarded waste stream.

UF membranes have also been used for the preparation of protein concentrates having reduced lactose content, from skim milk. Simple UF concentrates the protein, but leaves a product containing some lactose and salts, the content of which may be reduced by DF (see Ultrafiltration and Reverse Osmosis for the Dairy Industry, National institute for Dairy Research, Reading, England, 1985, p. 100). In the DF step, water is added at a rate which keeps protein concentration constant; it is undesirable to add water at a greater rate, because by keeping the lactose concentration high in the feed, it is removed at a relatively faster rate. In this example also, the permeating substances are of low value and can be discarded.

In many cases, it is desired to remove selected substances from aqueous stream, while imparting minimal changes to the remaining composition of the feed. However, the use of a washing/DF step in conjunction with selective, pressure driven process utilizing membranes has the drawbacks that large quantities of rinse water are required and that almost inevitably large quantities of feed components are lost through the selective membranes, and are not economically recoverable. Also, membranes with sharply defined selectivities are not available for many applications, while the use of less selective membranes tends to accentuate the losses of valuable solids.

Ionized organic substances can generally be removed from feeds by ED, of which examples are as follows:

(1) Smith et al (R & D Associates Convenience Food Conference, Philadelphia, 1964) reported the removal of citric acid from citrus juices and improvement of their organoleptic properties by ED; other workers reported similarly on the removal of a variety of organic acids from apple and citrus juices and from wines.

(2) Malic acid effluent containing less than 10% malic acid alone or in admixture with maleic and fumaric acids, when treated by ED, produces two streams, one of about 30% acid and the other less than about 0.3% (U.S. Pat. No. 3,752,749). In this case, the separation and concentration of acids is non-selective and the feed is relatively clean, being free of fouling agents which can clog the membranes and thus interfere with the separation process.

(3) The separation by ED of organic amino acid esters from admixtures with amphoteric amino acids is described in Israel Patent Nos. 52686 and 52687. In this case also, the feed is free of fouling agents.

Many industrial feed or waste streams may contain suspended or soluble substances which either adhere to the membrane pores or accumulate therein and thereby prevent efficient ion transfer. The problem of ED membrane fouling arises, for example, in demineralization of cheese whey (fouling by proteins), deacidification of citrus juices (fouling by high MW pectic substances) and demineralization of sugar molasses (fouling by proteins). Further, fouling may arise due to the presence of low and medium size molecules which adsorb strongly on and in the ED membranes; e.g., whereas organic anions MW<about 200 daltons are readily transported across anion exchange membranes, larger organic ions MW>about 450 are usually very problematic. Thus, the biodegradation product humic acid is present in most natural waters as colloidal negatively charged matter, and during ED such ions accumulate progressively on and in the membrane, and the electrical resistance of the ED stack is raised to the point where operation becomes uneconomical.

Various attempts have been made to overcome such difficulties, which would otherwise tend to delay or even prevent the penetration of ED technology into industrial and waste treatment fields.

Thus, in U.S. Pat. No. 4,554,076 there is described a method of modifying the surface of anion exchange membranes by coating with oriented layers of amphiphilic surface active molecules (having one polar and one hydrophilic end). This method does not have appeared to have been used on an industrial scale. Japanese Patent No. 1014234 (1980) describes the difficulties encountered in attempting to desalt sugar molasses streams, due to fouling of the (otherwise efficient) anion exchange membranes, and a solution of the problem by replacing the latter with a neutral porous layer of PVA, which reduces the efficiency of the process.

It is also known to pretreat the feeds to remove fouling substances, e.g. by use of UF to remove proteins and other contaminants prior to an ED step, but such processes have the following drawbacks:

(a) High extraction recoveries require high volumetric efficiencies of the UF/MF/RO step, which in turn means operation at high concentrations of fouling substances, i.e. low flux.

(b) If it is attempted to increase recovery without excessive concentration of the foulants, diafiltration or washing steps may be introduced. However, this leads to a diluted permeate, so that the economy of the subsequent ED step is impaired.

SUMMARY OF THE INVENTION

It is accordingly an object of the present invention to provide an efficient process and system for the removal of at least one organic acid from aqueous feed streams.

It is also an object of the present invention to provide the aforementioned process and system which would leave the ingredients of such aqueous feed streams substantially unchanged apart from the fact that at least one organic acid will have been removed.

It is still a further object of the present invention to provide a process and system of the type described in which the removal of at least one organic acid is effected by use of at least one electrodialysis membrane.

Yet another object of the invention relates to the use of electrodialysis membranes in the process and system of the type described in which such membranes are much less susceptible to fouling than in the comparable prior art.

Further objects of the invention will appear from the description which follows.

The present invention thus provides in one embodiment, a batch or continuous process for removing at least one organic acid from an aqueous feedstock comprising such acid, and for interim removal of at least one ingredient known to foul electrodialysis membranes, which comprises the steps of:
(i) subjecting the feedstock under superatmospheric pressure to the action of at least one selective nonelectrodialysis membrane adapted to retain the at least one fouling ingredient, the at least one selective nonelectrodialysis membrane being selected from the group consisting of selective ultrafiltration, microfiltration and reverse osmosis membranes, thereby to obtain (a) treated feedstock and (b) a permeate having a significantly reduced content of the at least one fouling ingredient and a substantially unchanged content of the at least one organic acid;
(ii) subjecting the permeate to treatment with at least one electrodialysis membrane, thereby to obtain (c) treated permeate from step (i) now having a significantly reduced content of the at least one organic acid, compared with such content of the initial aqueous feedstock, and (d) effluent; and
(iii) combining fractions (a) and (c) to give a product in which the content of water-soluble and water-insoluble ingredients is substantially unchanged, other than for the at least one organic acid.

It is preferred to operate the inventive process according to this embodiment, in such a manner that at least a part of (and more preferably, substantially the whole of) treated permeate (c) from step (ii) is recirculated so as to repeat at least step (ii) until stream (c) contains a concentration of the at least one organic acid which lies within a preselected range. In this preferred embodiment, recirculated treated permeate may be combined with fresh feedstock and the thus modified feedstock may be subjected to both steps (i) and (ii).

The process of the invention in this embodiment may for example be applied to the removal of at least one organic acid from citrus juices, or the removal of at least one organic acid comprising e.g. malic acid from green coffee extracts and other coffee streams.

In accordance with another embodiment, the present invention provides a continuous process for removing at least one species from an aqueous feedstock comprising such species, including contacting the feedstock with separation apparatus of first and second types, respectively, which comprises the steps of:
(i) subjecting the feedstock under superatmospheric pressure to the action of separation apparatus of a first type constituted by at least one selective reverse osmosis/ultrafiltration/microfiltration membrane adapted to retain at least one ingredient known to foul the second type of separation apparatus, thereby to obtain (a) treated feedstock and (b) a permeate having a significantly reduced content of the at least one ingredient and a substantially unchanged content of the at least one species;
(ii) subjecting the permeate to contact with the second type of separation apparatus adapted to remove the at least one species from the aqueous feedstock, thereby to obtain (c) treated permeate from step (i) now having a significantly reduced content of the at least one species, compared with such content of the aqueous feedstock and (d) effluent;
(iii) continuously recirculating substantially the whole of treated permeate (c) from step (ii) so as to repeat at least step (ii) until stream (c) contains a concentration of the at least one species which lies within a preselected range; and
(iv) combining fractions (a) and (c) to give a product in which the content of water-soluble and water-insoluble ingredients is substantially unchanged, other than for the at least one species.

This process embodiment may for example be applied to the removal of bitter components from fruit juice, so that recirculation step (iii) is repeated for the requisite number of times prior to step (iv), until the effluent (d) contains a concentration of the bitter components which lies within a preselected range. Moreover, this embodiment of the process of the invention may for example be applied also to the removal of at least one organic acid comprising e.g. malic acid from green coffee extracts and other coffee streams.

The invention further provides in accordance with another embodiment, a system for removing at least one species from an aqueous feedstock comprising such species, including contacting the feedstock with separation apparatus of first and second types, respectively, which comprises in operable combination: inlet feed apparatus for the feedstock; apparatus for pressurizing the feedstock to a superatmospheric pressure; apparatus for contacting the pressurized feedstock with separation apparatus of a first type constituted by at least one selective reverse osmosis/ultrafiltration/microfiltration membrane apparatus adapted to retain at least one ingredient known to foul the second type of separation apparatus; apparatus for removing treated pressurized feedstock from the membrane apparatus; apparatus for removing permeate from the membrane apparatus and for contacting it with the second type of separation apparatus adapted to remove the at least one species; apparatus for removing treated permeate from the second type of separation apparatus; apparatus for removing effluent from the second type of separation apparatus; and apparatus for combining the pressurized treated feedstock with the treated permeate.

The system of the invention preferably comprises additionally apparatus for recirculating at least a part of the treated permeate. Preferably also the system of the invention comprises monitoring apparatus for determining when the concentration of the at least one species lies within a preselected range, as well as control apparatus for terminating operation of the recirculating apparatus when the concentration of the undesired at least one species lies within a preselected range. The second type of separation apparatus may, e.g., comprise electrodialysis membrane apparatus, or it may comprise, e.g., ion exchange or absorption apparatus.

DETAILED DESCRIPTION OF THE INVENTION

Figure 1:
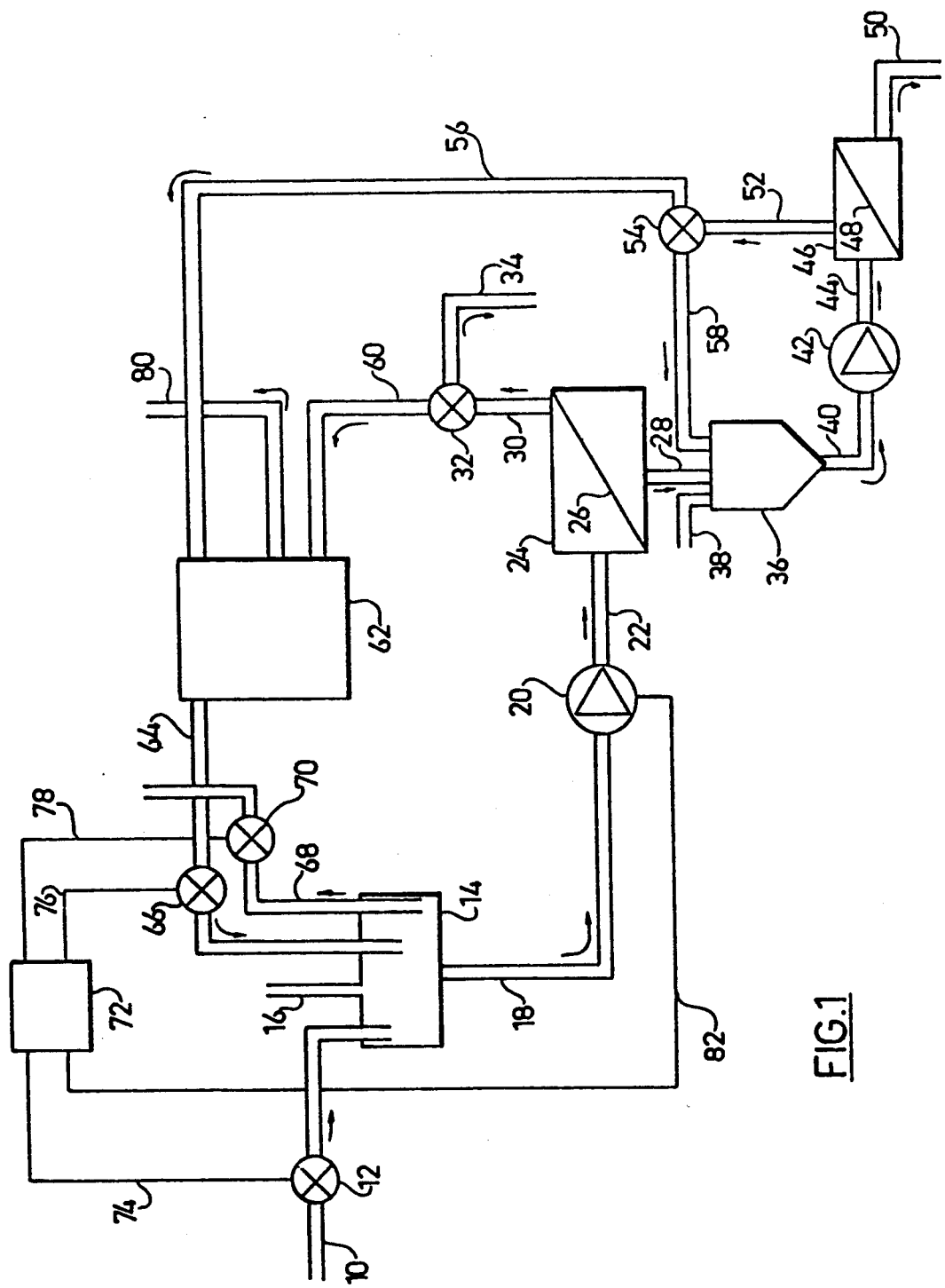
FIG. 1 illustates a particular embodiment of the present process and system.

In accordance with the present process, it will be appreciated that it is possible to mix incoming fresh feedstock with a relatively acid free stream from the electrodialysis step, thereby in effect obtaining a benefit of diafiltration without however diluting the feed and thus obviating an additional concentration step which would detract from the overall efficiency and economy of the process.

Thus in accordance with a particularly preferred embodiment of the invention, a continuous process for removing at least one organic acid from an aqueous feedstock comprising such acid, and for interim removal of at least one ingredient known to foul electrodialysis membranes, comprises carrying out the above-stated steps (i) and (ii), recirculating substantially the whole of the treated permeate (c) from step (ii) so as to be mixed with untreated aqueous feedstock and thus giving a modified aqueous feedstock which may be repeatedly subjected to steps (i) and (ii) until the concentration of the at least one organic acid in the thus-treated modified feedstock has fallen to a preselected level.

It will also be appreciated that since it is a general objective of the invention to recover the feedstock substantially unchanged apart from a significant reduction in the acid content, the ingredients which tend to foul the electrodialysis membrane are not undesirable in other respects and are not usually removed from the system as a whole, but rather they may be mixed with the other components of the system.

The selective membranes used to separate ED fouling ingredients may have sharp separation characteristics, which enable them to discriminate between molecules of rather close MW. For example, permeable species may have a MW of about 100-300, while the retained substances (including fouling ingredients) may have a MW of about 360-500, or higher.

In certain cases the separation between such closely related species to be separated can be sharpened by maintaining optimal pH in the feed. In one specific case of treating green coffee extracts (GCE) low MW organic acids such as citric acid (MW=210) and malic acid (MW=134) have to be extracted in the presence of another low MW foulant of ED, the chlorogenic acid (CAC), MW 360. The latter is a very strong foulant of anion exchange membranes assembled in the ED apparatus. Effective removal of (e.g.) malic acid can be readily achieved by ED (see U.S. Pat. No. 3,752,743), provided that the stream does not contain foulants; in the case of GCE, this removal can only be effectively achieved if CAC and other high and low MW foulants are eliminated from the stream to be contacted with the ED membranes.

By using selective reverse osmosis membranes ("SELRO") it is possible to effect a transport of organic acids such as malic acid into the permeate. The separation characteristics of the selective membranes can be imparted during the production of these membranes, but they may also be formed in situ by depositing from the feed a dynamic layer of artificially added or naturally existing polyelectrolytes during the RO step. It should be noted that the separation step at the RO membrane is a kind of diaextraction, insofar as the extraction may be regarded as being driven by diafiltration using internally recirculated permeate from the ED step. Use of a selective RO membrane is highly advantageous in comparison with the use of UF membranes, because in the latter case high MW species (which in any event will not be transported across the ED membrane) are mainly retained, whereas all the low MW species such as sugars, amino acids and vitamins are transported across the UF membranes and may be partially lost in the ED step. By contrast, since the selective RO membrane retains these low MW species to a certain degree, their loss in the ED step is minimized.

It is also to be stressed once again, that employment of a conventional diafiltration mode at the first (RO-/UF/MF) step would unduly dilute the permeate to be treated at the ED step, and make the removal of organic acids therefrom very difficult, if not impossible.

On the other hand, in accordance with an embodiment of the present invention, a selective diaextraction process is combined with continuous removal of organic acids. In the example of the removal of malic acid from GCE, a portion of the feed is contacted with a SELRO membrane which has tailor-made characteristics enabling retention of most of the CAC and a substantial proportion of the sugars; the permeate from which high and low molecular weight ED foulants have been removed is processed in the ED unit until the organic acid concentration has been reduced to a satisfactory (preselected) level. The thus-treated feed of the ED unit, from which most of the organic acid content has been removed, is continuously recycled into the feed of the SELRO unit so as to carry out what has been termed herein diaextraction, which is continued until it is feasible to withdraw a product in which the organic acid content has been reduced to an acceptable level.

As has already been intimated, the present invention is not limited to the use of ED; another selected process such as ion exchange or absorption may be used to permanently remove an undesired species from an aqueous feedstock. The permeate from the selective RO-/UF/MF step, after treatment for permanent removal of the undesired species, may be continuously recycled to effect further extraction of undesired species into the permeate.

For example, a continuous debittering process can be effected, in which a first RO/UF/MF step transforms a fraction of the feed volume into a foulant-free and depulped permeate, the permeate is subjected to a debittering process with resin-filled column, and the treated feed is continuously recycled back to the RO/UF/MF unit to effect further debittering. This process offers substantial advantages over the conventional process in which the whole juice volume is subjected to simple depulping, in order to minimize plugging of the absorption columns. Thus in the present process, there are no losses of the solubles beyond the amount of material which is adsorbed on the column, and since the latter is minimized as a result of retention of these substances in the preceding SELRO step, the total solute losses are minimized. Furthermore, the pulp composition which imparts to the juice its natural appearance is maintained unchanged, in the present process.

As previously noted generally, it is possible in this case to replace the SELRO membrane by selective UF or MF membranes, which would mainly effect depulping and removal of high MW solubles, thus facilitating debittering of the permeate in the subsequent absorption columns.

The advantages of the present invention will now be illustrated in the following non-limiting Examples.

EXAMPLE I

Removal of malic acid from aqueous streams in absence of fouling

An electrodialysis experiment was performed in a laboratory scale ED unit using an ED stack equipped with 8 anion exchange membranes Selemion from Asahi Glass, each of area $10 \times 3$ cm.$^2$. One liter of approx. 4% aqueous malic acid solution was processed in this unit by applying a current of 500 milliamperes at an established voltage of 30-40 volts, i.e. a voltage drop of approximately 3.5-5 volts/cell pair. The results are shown in Table 1; Table 2 shows results for a similar experiment where the initial malic acid concentration was 0.36%

TABLE 1

| time (mins.) | current (mA) | voltage (volts) | pH | malic acid (%) |
|---|---|---|---|---|
| 0 | 500 | 27 | 2.0 | 4.2 |
| 15 | 500 | 32 | 2.0 | 3.5 |
| 30 | 500 | 40 | 2.0 | 2.7 |
| 60 | 500 | 40 | 2.0 | 2.5 |

TABLE 2

| time (mins.) | current (mA) | voltage (volts) | pH | malic acid (%) |
|---|---|---|---|---|
| 0 | 300 | 32 | 2.5 | 0.36 |
| 30 | 300 | 47 | 3.0 | 0.12 |
| 60 | 300 | 57 | 4.0 | 0.03 |

These results show that the concentration of malic acid can be readily reduced to 300 ppm in absence of fouling agents.

EXAMPLE II

Behavior of chlorogenic acid (CAC)

An experiment was carried out under similar conditions to Example I, but substituting CAC for malic acid. The results are given in Table 3.

TABLE 3

| time (mins.) | current (mA) | voltage (volts) | CAC (%) |
|---|---|---|---|
| 0 | 50 | 58 | 1.25 |
| 60 | 80 | 58 | 1.18 |
| 120 | 100 | 58 | 1.18 |
| 180 | 100 | 58 | 1.18 |
| 300 | 100 | 58 | 1.18 |

These results show that introduction of CAC into the ED stack causes the voltage to increase to the limit of the current supply (58 volts), the current declines substantially, i.e. the resistance of the ED membranes is increasing as a result of poisoning by CAC. The latter cannot be removed from the feed by ED.

EXAMPLE III

Malic acid removal in presence of chlorogenic acid

An experiment was carried out under similar conditions to Example I. There were used one liter of aqueous solution containing malic acid (a) in absence of CAC and (b) in presence of 2.5% CAC. The results are given in Table 4.

TABLE 4

| time (mins.) | current (mA) | voltage (volts) | pH | malic acid (%) |
|---|---|---|---|---|
| (a): in absence of CAC | | | | |
| 0 | 300 | 38 | 2.0 | 0.54 |
| 15 | 300 | 54 | 2.5 | — |
| 30 | 300 | 54 | 3.0 | 0.28 | change of malic acid concentration: 0.26%
electrical efficiency of malic acid removal: 85%

| (b): in presence of 2.5% CAC | | | | |
|---|---|---|---|---|
| 0 | 250 | 58 | 2.5 | 0.38 |
| 15 | 220 | 58 | 2.0 | 0.28 |
| 30 | 220 | 58 | 2.5 | 0.19 | change of malic acid concentration: 0.19%
electrical efficiency of malic acid removal: 45%

The results demonstrate that in the presence of CAC the efficiency of malic acid removal is reduced almost by a factor of 2, and the resistance of the ED membranes increases (higher voltage at smaller current).

EXAMPLE IV

Malic acid removal from crude Green Coffee Extract

An experiment was carried out under similar conditions to Example I. There was used one liter of green coffee extract (GCE) prepared by mixing green coffee beans for a period of 1–2 hours with deionized water at 80° C. The GCE was then subjected to ED deacidification. The results are given in Table 5.

TABLE 5

| time (mins.) | current (mA) | voltage (volts) | malic acid (%) |
|---|---|---|---|
| 0 | 250 | 48 | 0.50 |
| 15 | 180 | 58 | 0.50 |
| 30 | 170 | 58 | 0.50 |
| 60 | 150 | 58 | 0.50 |
| 90 | 150 | 58 | 0.50 |
| 150 | 150 | 58 | 0.50 |

The results demonstrate that there is no removal of malic acid from the crude GCE stream despite the fact that it could readily be removed from corresponding non-fouling aqueous streams.

EXAMPLE V

Malic acid removal from crude Green Coffee Extract after pretreatment with a selective membrane An experiment was carried out under similar conditions to Example I. The feed for the ED membrane was in this instance a stream obtained as permeate by contacting green coffee extract (GCE) with a SELRO membrane in a RO apparatus. The characteristics of the SELRO membrane, which in a separate experiment (see Example 6, infra) is demonstrated to be capable of selectively transporting malic acid from an aqueos stream while retaining the CAC, are as shown in Table 6.

TABLE 6

| solute | concentration | MW | rejection |
|---|---|---|---|
| sodium chloride | 500 ppm | 58 | 20 |
| sodium chloride | 5% | 58 | 0 |
| sodium sulfate | 5% | 142 | 35 |
| sucrose | 1% | 360 | 95 |
| glucose | 1% | 180 | 70 |
| fructose | 1% | 180 | 70 |
| chlorogenic acid | 1% | 360 | 98 |
| anthocyanin (grape red color) | 1% | 900 | 99 |
| betaxanthine (red beet color) | 1% | — | 98 |
| sulfonated aromatics | 1% | 250 | 85 |
| sulfonated aromatics | 1% | 400 | 92 |
| sulfonated aromatics | 1% | 700 | 99 |
| sulfonated aromatics | 1% | 1000 | 99.99 |

The results of the ED experiment with the permeate of this SELRO membrane are given in Table 7.

TABLE 7

| time (mins.) | current (mA) | voltage (volts) | pH | malic acid (%) |
|---|---|---|---|---|
| 0 | 200 | 56 | 6.0 | 0.17 |
| 30 | 170 | 56 | 6.0 | 0.14 |
| 60 | 150 | 58 | 5.5 | 0.09 |
| 90 | 150 | 58 | 5.0 | 0.07 |
| 120 | 150 | 58 | 5.0 | 0.05 |
| 150 | 150 | 58 | 4.5 | 0.03 |

It is observed that more than 80% of the malic acid could be removed from the GCE after treatment with SELRO membrane. For comparison, the results of an ED experiment conducted with the permeate obtained after treatment with a UF membrane instead of SELRO, are given in Table 8. It is to be noted that in this case the process practically stops after the removal of 45% of the malic acid; also, the lowest value for malic acid concentration is 0.14%, compared with 0.03% for the SELRO permeate.

TABLE 8

| time (mins.) | current (mA) | voltage (volts) | pH | malic acid (%) |
| --- | --- | --- | --- | --- |
| 0 | 300 | 12 | 4.0 | 0.25 |
| 30 | 300 | 20 | 4.5 | 0.16 |
| 60 | 300 | 20 | 4.5 | 0.17 |
| 90 | 300 | 20 | 4.0 | 0.14 |
| 120 | 300 | 20 | 4.0 | 0.14 |
| 150 | 300 | 20 | 4.0 | 0.14 |

EXAMPLE VI

Selectivity of SELRO membrane towards malic acid and chlorogenic acid as a function of pH.

A membrane of area 8 cm.$^2$ was installed in a laboratory scale, magnetically stirred cell, filled with 150 ml. of deionized water containing 0.2% w/v each of analytical grade chlorogenic acid and malic acid. The pH of the solution was adjusted to different levels in the range of pH 2-5 by adding hydrochloric acid. The cell was pressurized by applying nitrogen at 25 atm., and 15 ml. permeate was collected, and analyzed by HPLC. The rejection values of the membrane for each solute were calculated from the measured concentration values in the permeate and the feed by the following equation:

$$R(\%) = (1 - Cp/Cf) \times 100.$$

The results are summarized in Table 9, below. It will be observed that the relative transport of malic acid vs. chlorogenic acid is pH dependent and the diafiltration at an optimal point will enable the recovery of most of the malic acid (MA), with minimal losses of chlorogenic acid (CAC) into the permeate.

TABLE 9

| pH | R(%) CAC | R(%) MA | relative permeation: 100-R (MA)/100-R (CAC) |
| --- | --- | --- | --- |
| 5 | 89 | 60.9 | 3.6 |
| 4 | 90 | 62.5 | 3.8 |
| 3 | 79.5 | 61.6 | 1.9 |
| 2 | 77.5 | 40.4 | 2.6 |

EXAMPLE VII

Deacidification of citrus juices using "diaextraction"

The diaextraction system illustrated schematically in FIG. 1, in which liquid is circulated in the direction indicated by the arrows, was used for the deacidification of orange juice. Whole orange juice containing 12% pulp, 11 Brix sugar and 1.5% acids was fed at an exemplary rate of 100 l./hr. via inlet conduit 10 and valve 12 into feed tank 14 (vented to atmospheric pressure at 16); the juice was circulated from feed tank 14 via conduit 18 and thence through conduit 22 by means of centrifugal pump 20 to microfiltration module 24 containing a microfiltration (MF) membrane 26 of area 1 m.$^2$ at a linear velocity of 4 m./sec. The MF membrane had 5 micron pores. Treated feedstock may be removed from the module via exit conduit 30 and valve 32, and may be bled from the system (if desired) by conduit 34. The clarified permeate issues from module 24 via conduit 28; it had a soluble solids content close to that of the original feed juice, but its pulp content was below 0.5%. This depulped juice was fed first to tank 36 which is vented to atmospheric pressure at 38, and from there via conduit 40, pump 42 and conduit 44 to be deacidified in unit 46 which contains ED membranes 48. Citric acid is removed from the unit 46 via exit conduit 50. The concentration of citric acid in the depulped juice, measured in tank 36 declined with time as shown in Table 10. It will be appreciated that in general, progressively deacidified juice, previously depulped, may be withdrawn from unit 46 via conduit 52 and valve 54, and recirculated to tank 36 for further treatment at the ED membranes until a preselected level of acidity is reached.

TABLE 10

| time (mins.) | citric acid (%) |
| --- | --- |
| 0 | 1.5 |
| 30 | 1.0 |
| 60 | 0.7 |
| 90 | 0.3 |
| 120 | 0.2 |

After reaching a citric acid concentration of 0.2%, the depulped and deacidified stream was withdrawn from the ED unit 46 via conduit 52, valve 54 and conduit 56 to intermediate tank 62, there to be mixed with treated feedstock from microfiltration module 24, which reaches the intermediate tank via conduit 30, valve 32 and conduit 60. From the intermediate tank, the mixture which is effectively reconstituted deacidified juice may be withdrawn from the system if desired, via conduit 80, but in the present example it is recirculated via conduit 64 and valve 66 into feed tank 14, at a flow rate which was identical to the permeate flow rate of ∼500 l./hour. After about 60 minutes the acid concentration in the feed tank had reduced from 1.5% to 0.5%, thus improving the brix to acid value from 7.3 originally, to 22. At this point, a continuous supply of fresh orange juice is fed into tank 14 via conduit 10 and valve 12, at a rate of 200 l. per hour and simultaneously, deacidified but otherwise reconstituted juice (with the original pulp content) is bled from the system via conduit 68 and valve 70.

It will be appreciated that the rate of feeding and mixing of the various fractions of juice may be controlled in a manner known per se. Thus, for example, the amounts of liquid passing through valves 12, 66 and 70, and pump 20, may be monitored at control box 72 which may include (e.g.) a microprocessor (not shown), by information fed through two-way conductive lines 74, 76, 78 and 82, respectively, and the control box may output through these lines to control the amounts of the respective liquids passing through these valves and pump 20. Thus, by way of example, control box 72 may be preset to keep the liquid level in tank 14 constant, i.e. the total volume of liquid per unit time passing through valves 12 and 66 into the tank may substantially equal the total volume of liquid per unit time withdrawn from the tank via valve 68 and conduit 18. Of course, the water removed with the undesired acid content of the juice via conduit 50 may be compensated for by addition of a similar amount of water to tank 14, by means not shown; and the amount of water thus added may be controlled from box 72 by means not depicted in the figure, and therefore may be accounted for in the liquid balance of the overall operation, if desired.

Those skilled in the art will appreciate that many modifications and variations may be effected in the practice of the invention, and therefore the latter is not to be regarded as limited to the methods of operation particularly described. Rather, the scope of the invention will be defined with reference to the claims which follow.

We claim:

1. A process for removing at least one dissolved non-fouling organic acid known not to foul electrodialysis membranes from an aqueous feedstock comprising such acid, and for interim removal of at least one dissolved fouling ingredient known to foul electrodialysis membranes, which comprises the steps of:

(i) subjecting said feedstock under superatmospheric pressure to the action of at least one selective non-electrodialysis membrane adapted to retain said at least one dissolved fouling ingredient while allowing the passage therethrough of said at least one dissolved non-fouling organic acid, said at least one selective non-electrodialysis membrane being a selective reverse osmosis membrane having pores within the range of 0.1 to 1.0 nanometers, thereby to obtain (a) treated feedstock and (b) a permeate having a significantly reduced content of said at least one dissolved fouling ingredient and a substantially unchanged content of said at least one dissolved non-fouling organic acid;

(ii) subjecting said permeate to treatment with at least one electrodialysis membrane, thereby to obtain (c) treated permeate from step (i) now having a significantly reduced content of said at least one dissolved non-fouling organic acid, compared with such content of said aqueous feedstock, and (d) effluent; and (iii) combining fractions (a) and (c) to give a product in which the content of water-soluble and water-insoluble ingredients is substantially unchanged, other than for said at least one dissolved non-fouling organic acid.

2. A process according to claim 1, which is operated as a batch process.

3. A process according to claim 1, which is operated as a continuous process.

4. A process according to claim 1, wherein at least a part of treated permeate (c) from step (ii) is recirculated so as to repeat at least step (ii) until stream (c) contains a concentration of the at least one dissolved non-fouling organic acid which lies within a preselected range.

5. A process according to claim 4, wherein said treated permeate (c) from step (ii) is thus recirculated, while combining with fresh aqueous feedstock giving a modified aqueous feedstock which is repeatedly subjected to steps (i) and (ii) until the concentration of the at least one dissolved non-fouling organic acid in the thus-treated modified feedstock has fallen to a preselected level.

6. A process according to claim 1, which is applied to the removal of at least one dissolved non-fouling organic acid from citrus juices.

7. A process according to claim 1, which is applied to the removal of at least one dissolved non-fouling organic acid from at least one stream selected from the group consisting of green coffee extracts and other coffee streams.

8. A process according to claim 7, wherein the at least one dissolved non-fouling organic acid comprises malic acid.

9. A process according to claim 8, wherein said dissolved fouling ingredient comprises chlorogenic acid.

10. A continuous process for removing at least one dissolved species from an aqueous feedstock comprising such species, including contacting said feedstock with separation means of first and second types, respectively, which comprises the steps of:

(i) subjecting said feedstock under superatmospheric pressure to the action of separation means of a first type constituted by at least one selective reverse osmosis membrane having pores within the range of 0.1 to 1.0 nanometers adapted to retain at least one dissolved ingredient known to foul said second type of separation means while allowing the passage therethrough of said at least one dissolved species, thereby to obtain (a) treated feedstock and (b) a permeate having a significantly reduced content of said at least one dissolved ingredient and a substantially unchanged content of said at least one dissolved species;

(ii) subjecting said permeate to contact with said second type of separation means adapted to remove said at least one dissolved species from said aqueous feedstock, thereby to obtain (c) treated permeate from step (i) now having a significantly reduced content of said at least one dissolved species, compared with such content of said aqueous feedstock, and (d) effluent;

(iii) continuously recirculating treated permeate (c) from step (ii) so as to repeat at least step (ii) until stream (c) contains a concentration of the at least one dissolved species which lies within a preselected range; and (iv) combining fractions (a) and (c) to give a product in which the content of water-soluble and water-insoluble ingredients is substantially unchanged, other than for the at least one dissolved species.

11. A process according to claim 10, wherein treated permeate (c) is, prior to or after recirculation, combined with fresh aqueous feedstock giving a modified aqueous feedstock which is repeatedly subjected to steps (i) and (ii) until the concentration of the at least one dissolved species in the thus-treated modified feedstock has fallen to a preselected level.

12. A process according to claim 10, which is applied to the removal of bitter components from fruit juice.

13. A process according to claim 10, which is applied to the removal of at least one organic acid from at least one stream selected from the group consisting of green coffee extracts and other coffee streams.

14. A process according to claim 13, wherein the at least one organic acid comprises malic acid.

15. A process according to claim 13, wherein said at least one organic acid comprises malic acid which is removed in presence of said dissolved ingredient comprising chlorogenic acid.

16. A process for removing malic acid from an aqueous feedstock selected from green coffee extracts and other coffee streams, which aqueous feedstock contains both dissolved malic acid and dissolved chlorogenic acid, and for interim removal of said dissolved chlorogenic acid, which process comprises the steps of:

(i) subjecting said feedstock under superatmospheric pressure to the action of at least one selective reverse osmosis membrane effective to retain chlorogenic acid while allowing the passage therethrough of malic acid, thereby to obtain (a) treated feedstock and (b) a permeate having a significantly reduced content of chlorogenic acid and a substantially unchanged content of malic acid;

(ii) subjecting said permeate to treatment with at least one electrodialysis membrane, thereby to obtain (c) treated permeate from step (i) now having a significantly reduced content of malic acid, compared with such content of said aqueous feedstock, and (d) effluent; and (iii) combining fractions (a) and (c) to give a product in which the content of water-soluble and water-insoluble ingredients is substantially unchanged, other than for malic acid.

17. A process according to claim 16, wherein at least a part of treated permeate (c) from step (ii) is recirculated so as to repeat at least step (ii) until stream (c) contains a concentration of malic acid which lies within a preselected range.

18. A process according to claim 17, wherein said treated permeate (c) from step (ii) is thus recirculated, while combining with fresh aqueous feedstock giving a modified aqueous feedstock which is repeatedly subjected to steps (i) and (ii) until the concentration of malic acid in the thus-treated modified feedstock has fallen to a preselected level.

19. System for removing malic acid from an aqueous feedstock selected from green coffee extracts and other coffee streams, which aqueous feedstock contains both dissolved malic acid and dissolved chlorogenic acid, which comprises in operable combination:

inlet feed means for said feedstock;

means for pressurizing said feedstock to a superatmospheric pressure;

means for contacting said pressurized feedstock with at least one selective reverse osmosis membrane means effective to retain chlorogenic acid while allowing the passage therethrough of malic acid;

means for removing treated pressurized feedstock from said membrane means;

means for removing permeate from said membrane means and for contacting it with separation means adapted to remove malic acid;

means for removing treated permeate from said separation means;

means for removing effluent from said separation means; and means for combining said pressurized treated feedstock with said treated permeate.

20. System according to claim 19 which comprises additionally:

means for recirculating at least a part of said treated permeate so as to subject it to further contact with at least said second type of separation means.

21. System according to claim 19 which further comprises:

monitoring means for determining when the concentration of malic acid lies within a preselected range, and control means for terminating operation of said recirculating means when the concentration of malic acid lies within a preselected range.

22. System according to claim 19 which also comprises:

means for admixing treated permeate with fresh feedstock and means for circulating the thus-obtained admixture serially to contact with both said selective reverse osmosis membrane means and said separation means.

23. System according to claim 19, wherein said separation means comprises electrodialysis membrane means.

24. System according to claim 19, wherein said second type of separation means comprises ion exchange or absorption means.

* * * * *